US010792079B1

(12) United States Patent
Hamade

(10) Patent No.: US 10,792,079 B1
(45) Date of Patent: Oct. 6, 2020

(54) SURGICAL TOOL

(71) Applicant: Wael Hamade, Pittsburgh, PA (US)

(72) Inventor: Wael Hamade, Pittsburgh, PA (US)

(*) Notice: Subject to any disclaimer, the term of this patent is extended or adjusted under 35 U.S.C. 154(b) by 0 days.

(21) Appl. No.: 16/907,273

(22) Filed: Jun. 21, 2020

(51) Int. Cl.
*A61B 17/70* (2006.01)

(52) U.S. Cl.
CPC ...... *A61B 17/7082* (2013.01); *A61B 17/7091* (2013.01)

(58) Field of Classification Search
CPC ............ A61B 17/7082; A61B 17/8877; A61B 17/888
See application file for complete search history.

(56) References Cited

U.S. PATENT DOCUMENTS

| | | | | | |
|---|---|---|---|---|---|
| 3,963,199 A | * | 6/1976 | Pravaz | .......... | B64D 17/46 244/148 |
| 5,033,740 A | * | 7/1991 | Schwartz | .......... | A63B 21/072 482/105 |
| 6,247,739 B1 | * | 6/2001 | Lyon | .......... | A45F 5/1026 294/137 |
| 8,784,431 B1 | * | 7/2014 | Harder | .......... | A61B 17/7082 606/104 |
| 2010/0331151 A1 | * | 12/2010 | Signorile | .......... | A63B 21/0728 482/93 |
| 2011/0312477 A1 | * | 12/2011 | Wiseman | .......... | A63B 21/0552 482/126 |
| 2014/0100616 A1 | * | 4/2014 | Shipp | .......... | A61B 17/7082 606/86 A |
| 2015/0201987 A1 | * | 7/2015 | Lemoine | .......... | A61B 17/8891 606/104 |
| 2015/0250521 A1 | * | 9/2015 | Poker | .......... | A61B 17/888 606/104 |

\* cited by examiner

*Primary Examiner* — Nicholas W Woodall
(74) *Attorney, Agent, or Firm* — Barry Choobin; Patent 360

(57) ABSTRACT

The present invention is directed to a surgical tool and a method of use thereof. The surgical includes a rod having opposite ends, the rod configured to be received into a rod-receiving portion of a head of a pedicle screw; a pair of elongated arms each having a proximal end and a distal end, the pair of elongated arms at proximal ends coupled to the opposite ends of the rod; and a handle connects the distal ends of the pair of elongated arms, the handle having a second length, the handle shaped to be grabbed by a hand.

13 Claims, 3 Drawing Sheets

US 10,792,079 B1

SURGICAL TOOL

FIELD OF INVENTION

The present invention generally relates to a surgical tool, and in particular, the present invention relates to a surgical tool for removing pedicle screws and lateral mass screws.

BACKGROUND

Pedicle screws are used for spinal stabilization. There are different type of polyaxial bone screws that are designed for implantation into a vertebral body. The pedicle screws are used during spinal surgery for stabilization. Pedicle screws are used for both lumbar and cervical spine stabilization. The Pedicle screws typically include a threaded shank that is adapted to be screwed into a pedicle of the vertebra using a specialized screwdriver. One end of the threaded shanks having a sharp tip while the other end having a swivel head. A U-shaped slot is formed in the head for receiving the rod. The rod connects at least two adjacent pedicle screws, wherein the swivel head facilitates alignment and seating of a rod. The head has threads in the rod receiving portion to receive a cap, wherein tightening the cap locks the rod in place.

Pedicle screws are commercially available from a range of manufacturers. There are no universal screwdrivers for screwing and unscrewing the pedicle screws. Pedicle screws from different manufacturers may require a different screwdriver. There are currently over 200 spine companies in the US, and combined, have thousands of different screw systems. These spine companies have to differentiate their products from other competitors. One of the many ways to do that is by having unique screw to screwdriver interface. For example, company "A" may have screws with a hex interface while company "B" may have screws with a star interface.

With virtually thousands of options for screws, a major problem occurs with the fact that surgeons are unable to get the specific screwdriver to remove screws. This happens for many reasons. One reason for example, is that there is no documentation for what the original hardware is. Another reason could be the original hardware implanted is so old that it has been rendered obsolete. Another reason could be that a patient comes in for an emergency trauma and there simply isn't anytime to acquire the necessary screwdriver. These reasons cause significant delays in surgery and can potentially negatively impact patient outcomes.

Thus, a need is appreciated for a universal screwdriver for unfastening the pedicle screws.

SUMMARY OF THE INVENTION

The principal object of the present invention is therefore directed to a surgical tool for removing pedicle screws.

It is a further object of the present invention that the same surgical tool can be used to remove pedicle screws of different manufacturers.

It is an additional object of the present invention that the surgical tool is easy to use.

It is still an additional object of the present invention that the surgical tool is economical to manufacture.

In one aspect, the present invention is directed to a surgical tool for removing pedicle screws from vertebrae during spinal surgery. The surgical tool comprises a rod configured to be received into the rod-receiving portion of the head of the pedicle screw. The rod having a first length. A pair of elongated arms each having a proximal end and a distal end. The pair of elongated arms at their proximal ends coupled to the opposite ends of the rod. The pair of elongated arms extend in the same plane. A handle, shaped to be grasped by the hand, is coupled at its opposite ends to the distal ends of the pair of elongated arms. The handle is having a second length. The second length is more than the first length. Each elongated arm is of an arc shape, wherein the pair of arms curve outwards from the proximal end towards the distal end.

In one aspect, the present invention is a method of removing the pedicle screws from the vertebrae during spinal surgery. The method comprising removing a cap of the pedicle screw. Thereafter, removing the aligning rods from the head. The surgical tool at its rod part can be positioned into the rod-receiving portion of the head. Once the rod of the surgical tool is in place, the cap can be re-tightened. Thereafter, the surgical tool can be grasped by the handle and rotated counterclockwise to unfasten the pedicle screw.

These and other objects and advantages of the embodiments herein will become readily apparent from the following detailed description.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
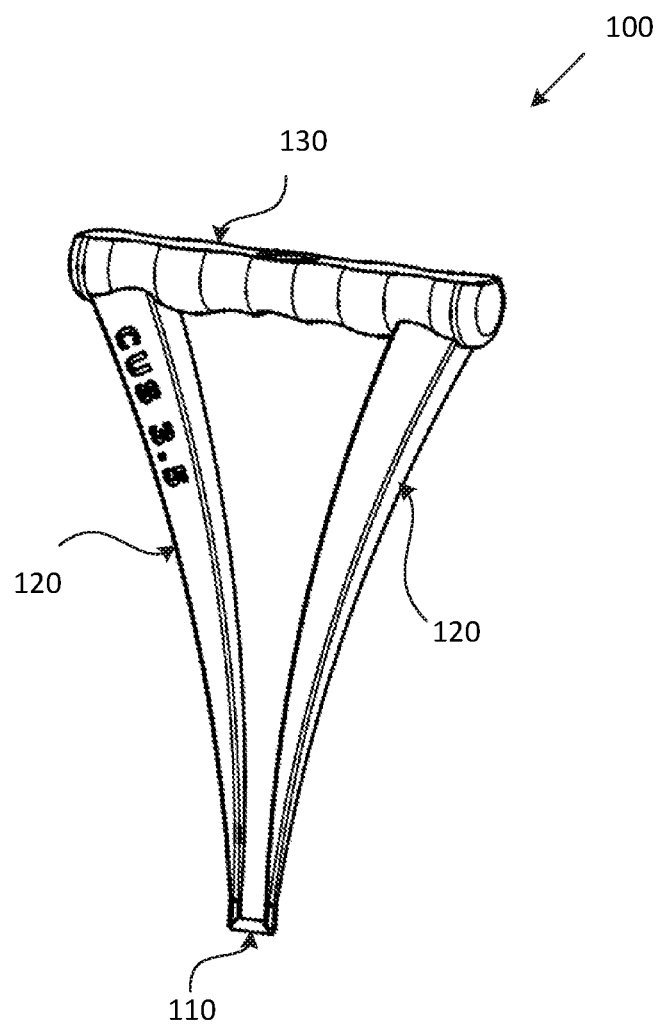
FIG. 1 shows a surgical tool for removing cervical pedicle screws, according to an exemplary embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as devices and methods of use thereof. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

The following detailed description is described with reference to the drawings, wherein like reference numerals are used to refer to like elements throughout. In the following description, for purposes of explanation, specific details may be set forth in order to provide a thorough understanding of the subject innovation. It may be evident, however, that the claimed subject matter may be practiced without these specific details.

The present invention is directed to a surgical tool for removing pedicle screws from vertebrae during spinal surgery. Referring to FIG. 1, the surgical tool 100 includes a rod 110 that is shaped to be received into a rod-receiving portion of the head of the pedicle screw. The surgical tool 100 further includes a pair of arms 120 each having a proximal end and a distal end. The rod 110 at its ends is coupled to the proximal ends of the pair of elongated arms 120. The distal ends of the pair of arms 120 are coupled to the ends of a handle 130. In one implementation, the rod can be of a diameter ranging from about 3 mm to 7 mm.

In one implementation, surgical tool 100 is designed to remove posterior cervical screws that were implanted during spine surgery in the cervical and upper thoracic area. The overall length of the surgical tool 100 is about 194.4 mm long. The handle 130 is about 130 mm in length. The width of the handle 130 is about 24 mm. The rod 110 at the bottom of the surgical tool is about 3.5 mm diameter and about 14 mm in length. The inner length of the rod 110 is about 9 mm. Each arm 120 is about 2.5 mm in width. This surgical tool can be used to remove the pedicle screws regardless of the screw design. The pedicle screws that can receive a 3.5 mm diameter rod can be removed by the surgical tool 100.

Figure 2:
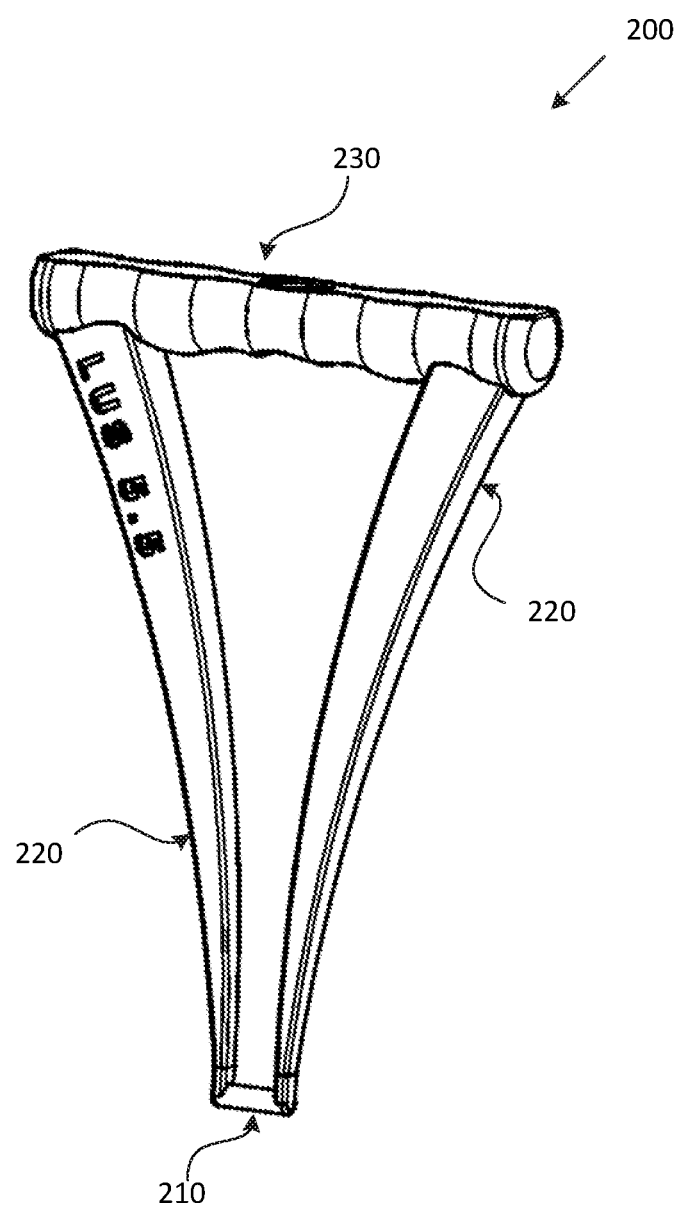
FIG. 2 shows a surgical tool for removing lumbar pedicle screws, according to an exemplary embodiment of the present invention.

FIG. 2 shows another implementation of the surgical tool 200 that can be used to remove the pedicle screws that were implanted during spine surgery in the thoracic and lumbar area. The surgical tool 200 having the rod 210, a pair of arms 220 and a handle 230. The overall length of this surgical tool 200 is about 195.4 mm long. The handle 230 is about 130 mm long. The width of the handle 230 is about 24 mm. The rod 210 at the bottom of the surgical tool is about 5.5 mm diameter and about 20 mm in length. The inner length of the rod is about 13 mm. Each arm is about 3.5 mm in width. This surgical tool 200 is intended to function regardless of screw design (so long as it accommodates a 5.5 mm rod diameter). This surgical tool will remove the tedious task of trying to find one of several different spine companies and locate their exact screwdriver for their exact system to remove the screw.

Figure 3:
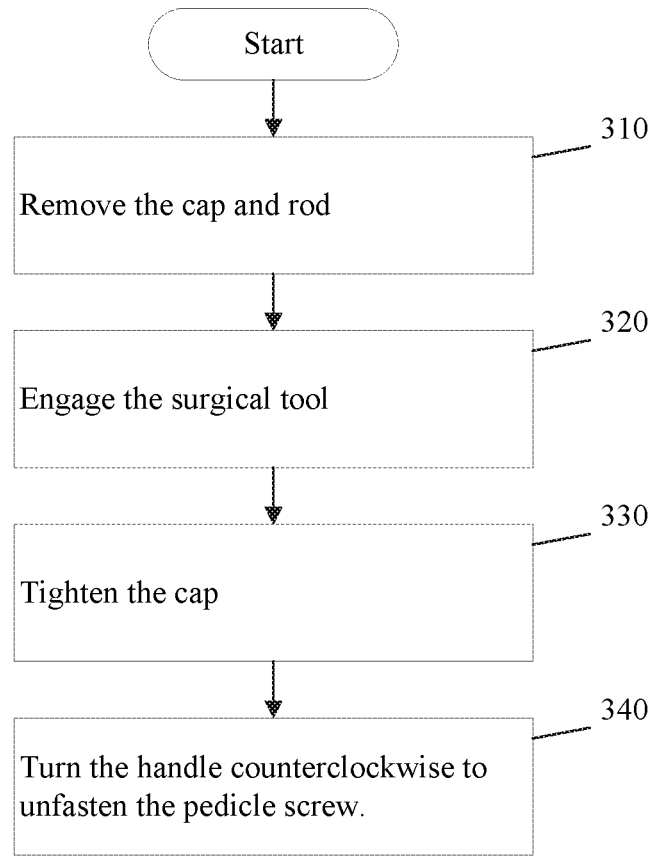
FIG. 3 shows a method of removing the pedicle screws, according to an exemplary embodiment of the present invention.

FIG. 3 shows a method of removing the pedicle screws in typical spine surgery. At step 310, the cap and rod already fixed to the pedicle screws can be removed to access the screw. At step 320, the rod portion of the surgical tool can be inserted into the tulip head of the pedicle screw. Thereafter, at step 330, the removed cap can be inserted back into the tulip head over the rod of the surgical tool. Once tightened, the handle can be turned counterclockwise to remove the screw, at step 340.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A surgical tool comprising:
   a rod having opposite ends, the rod configured to be received into a rod-receiving portion of a head of a pedicle screw, the rod having a first length and a diameter;
   a pair of elongated arms each having a proximal end and a distal end, the pair of elongated arms at the proximal ends coupled to the opposite ends of the rod;
   a handle connects the distal ends of the pair of elongated arms, the handle having a second length, the handle shaped to be grabbed by a hand; and
   wherein the rod is cylindrical having the diameter in a range of 3.0 to 7.0 mm.

2. The surgical tool of claim 1, wherein the rod is cylindrical having the diameter in a range of 3.5 to 5.5 mm.

3. The surgical tool of claim 1, wherein the second length of the handle is more than the first length of the rod.

4. The surgical tool of claim 3, wherein each of the pair of arms curve outwards from the proximal end towards the distal end.

5. The surgical tool of claim 4, wherein each arm is of an arc-shaped having a narrow curvature from the proximal end up to middle and a broad curvature from the middle up to the distal end.

6. The surgical tool of claim 1, wherein the first length of the rod is about 14 mm and the second length of the handle is about 130 mm.

7. The surgical tool of claim 2, wherein the first length of the rod is about 20 mm and the second length of the handle is about 130 mm.

8. The surgical tool of claim 1, wherein width of each of the pair of elongated arms increases from the proximal end towards the distal end.

9. A method of removing a pedicle screw comprising the steps of:
   removing a cap and an aligning rod from head of the pedicle screw;
   providing a surgical tool, the surgical tool comprises:
      a rod having opposite ends, the rod configured to be received into a rod-receiving portion of the head of the pedicle screw, the rod having a first length and a diameter,
      a pair of elongated arms each having a proximal end and a distal end, the pair of elongated arms at the proximal ends coupled to the opposite ends of the rod,
      a handle connects the distal ends of the pair of elongated arms, the handle having a second length, the handle shaped to be grabbed by a hand;
   engaging the rod of the surgical tool into a rod-receiving portion of the head of the pedicle screw;
   tightening the cap into the head of the pedicle screw; and
   turning the handle of the surgical tool counterclockwise.

10. The method of claim 9, wherein the rod is cylindrical in shape having the diameter in a range of 3.0 to 7.0 mm.

11. The method of claim 9, wherein the rod is cylindrical in shape having the diameter in a range of 3.5 to 5.5 mm.

12. The method of claim 9, wherein the second length of the handle is more than the first length of the rod.

13. The method of claim 12, wherein each arm is of an arc-shaped having a narrow curvature from the proximal end up to middle and a broad curvature from the middle up to the distal end.

* * * * *